United States Patent [19]

Ryer et al.

[11] 4,263,154

[45] Apr. 21, 1981

[54] MULTIFUNCTIONAL THIOCYANATE AMINE SALT ADDITIVE FOR FUELS AND LUBRICATING OILS AND COMPOSITIONS CONTAINING SAID ADDITIVE

[75] Inventors: Jack Ryer, East Brunswick; Salvatore J. Girgenti, Westfield; Esther D. Winans, Colonia, all of N.J.

[73] Assignee: Exxon Research & Engineering Co., Florham Park, N.J.

[21] Appl. No.: 91,691

[22] Filed: Nov. 5, 1979

[51] Int. Cl.$^3$ .................... C10M 1/38; C07C 161/02
[52] U.S. Cl. .................................. 252/47.5; 260/454
[58] Field of Search ....................... 260/454; 252/47.5

[56] References Cited

U.S. PATENT DOCUMENTS

| | | | |
|---|---|---|---|
| 1,841,458 | 1/1932 | Taube | 260/454 |
| 2,642,353 | 6/1953 | Mowry et al. | 260/454 |
| 3,179,591 | 4/1965 | Herbert | 252/47.5 |
| 3,231,623 | 1/1966 | Reifschneider et al. | 260/454 |
| 3,330,763 | 7/1967 | Damrath | 252/47.5 |

OTHER PUBLICATIONS

Noller, Textbook of Organic Chemistry, W. B. Saunders, New York, 1968, p. 249.

*Primary Examiner*—Henry R. Jiles
*Assistant Examiner*—Robert E. Whittenbaugh
*Attorney, Agent, or Firm*—Roland A. Dexter; John J. Mahon

[57] ABSTRACT

This invention relates to a hydrocarbon-soluble sulfur-nitrogen compound resulting from the reaction of a dialkyl-4-hydroxy benzyl thiocyanate and a $C_{12}$—$C_{24}$ alkyl primary amine which compounds have utility as multifunctional, i.e. antioxidation, antiwear, extreme pressure and lubricity modification, additive for fuels and lubricants.

7 Claims, No Drawings

MULTIFUNCTIONAL THIOCYANATE AMINE SALT ADDITIVE FOR FUELS AND LUBRICATING OILS AND COMPOSITIONS CONTAINING SAID ADDITIVE

BACKGROUND OF THE INVENTION

1. Field of the Invention

This invention relates to sulfur- and nitrogen-containing compositions and in a more particular sense it relates to those compounds having a thiocyanate salt/thiourea moiety adapted for use as a multifunctional additive in hydrocarbons. This invention relates also to hydrocarbon fuels and oils, especially lubricating oil compositions containing said multifunctional sulfur- and nitrogen-containing compositions.

2. General Background

The problem of deterioration of hydrocarbons has been the cause of principal concern in the formulation of hydrocarbon compositions such as fuels and lubricating compositions. Deterioration of hydrocarbons results in the formation of products which are corrosive to the metal surfaces with which the hydrocarbons come into contact.

In recent years it has been a common practice to incorporate into lubricating oils chemical additives which are capable of inhibiting the deterioration of oil and the formation of these harmful deposits. Such additives have generally been classified into various groups according to the manner in which they function to improve hydrocarbon oil. One group of such additives are the oxidation inhibitors which function to stabilize the oil against oxidative degradation. Another group of such additives are the corrosion inhibitors which counteract the corrosiveness of the products of oil degradation or passivate the metal surfaces against the corrosive action of such products. Still another group of such additives are the extreme pressure agents which function to enhance the load-carrying ability of the oil and thereby prevent or at least reduce the abrasive friction between the moving lubricated surfaces.

Two or more additives are often needed in a hydrocarbon fuel or oil to stabilize the hydrocarbon against formation of harmful degradation products. The incorporation of several different types of additives not only is costly, but is also dependent upon the compatibility of the additives with one another. Thus, it is known that additives which are effective separately may not be used in combination because of their incompatibility. A great deal of effort has recently been devoted to the development of so-called "multifunctional" additive, i.e., an additive which, by itself, is capable of imparting several desirable properties to a hydrocarbon fuel or oil. It will be readily appreciated that the use of such additive is highly advantageous from the standpoint of both economy and convenience.

3. Prior Art Publications

Sulfur- and nitrogen-containing compositions are stated to provide such desirable multifunctional activity to both fuels and lubricating oils. For example, in U.S. Pat. Nos. 2,619,464 and 2,680,759 it is reported that mineral lubricating oils containing small amounts of high molecular weight alkyl monothiocyanates, preferably $C_{21}$–$C_{34}$ monothiocyanates as paraffin wax monothiocyanates, are resistant to oxidation and have a reduced tendency to corrode hard metal alloy bearings; and, 3,330,763 discloses the use of hydrocarbylamine salts of thiocyanic acid as load-carrying additives in lubricating oils.

It is, accordingly, an object of this invention to provide novel compositions of matter.

It is also an object of this invention to provide compositions adapted for use as multifunctional additives in hydrocarbons, particularly for fuels and oils.

It is also an object of this invention to provide compositions useful as corrosion, oxidation inhibitors and/or dispersants in hydrocarbon lubricating oils.

SUMMARY OF THE INVENTION

In U.S. Patent Application Ser. No. 74,821 filed Sept. 12, 1979 of common assignee, it has been reported that an allylic thiocyanate resulting from the reaction of an alkenyl halide with potassium thiocyanate is, after isomerization to an isothiocyanate, susceptible to derivatization with protoic reactants, particularly upon reaction with: amines, preferably alkylene polyamines: alcohols, preferably polyols; thiols; and, mixtures thereof to yield thiocarbamyl derivatives having activity in hydrocarbons, particularly fuels and lubricating oils.

It has now been discovered that a dialkyl-4-hydroxybenzyl thiocyanate can be reacted with an alkyl primary amine containing from 12 to 24 total carbons to yield a hydrocarbon-soluble thiocyanate salt/thiourea having the multifunctional properties of enhancing the oxidation resistance-antiwear-extreme pressure resistance of hydrocarbon fuels and oils as well as providing lubricity improvement.

The thiocyanato salt/thiourea additive of the invention is obtained by the equimolar reaction of an alkyl (preferably t-alkyl) primary amine having 12 to 24, preferably 16 to 20, total carbons with a 4-hydroxy-dialkyl substituted benzyl thiocyanate (included is any in situ isomerization to the corresponding isothiocyanate) usually at a temperature of from 0° C. to 200° C., preferably 30° to 100° C., and for a period of from 0.5 to 24, preferably 1 to 10 hours.

In accordance with this invention there is provided a composition comprising a liquid hydrocarbon usefully a fuel or lubricating oil having dissolved therein a minor but at least antiwear amount of a hydrocarbon-soluble sulfur-nitrogen-containing additive characterized as a $C_{12}$–$C_{24}$ primary amine 4-hydroxy-dialkyl benzyl thiocyanato salt/thiourea; said amount being generally from 0.01 to 20, preferably 0.3 to 3.0 wt.% of the total lubricating oil composition and being usually from 4 to 20 parts per million of the total weight of the fuel.

DETAILED DESCRIPTION OF THE INVENTION

The preparation of the hydrocarbon-soluble thiocyanato salt/thiourea of the invention involves: firstly, a reaction of a hydroxy dialkyl benzyl alcohol with at least an equal molar proportion of an inorganic thiocyanate salt; followed, by a second reaction with an alkylated primary amine.

Hydroxy Dialkyl Benzyl Chloride

The hydroxy dialkyl benzyl chlorides for the purpose of this invention conform to the formula

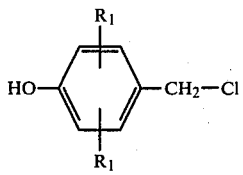

wherein $R_1$ and $R_2$ are the same or different $C_1$ to $C_4$ alkyl groups, e.g. methyl, ethyl, butyl with t-butyl preferred and propyl. The aforesaid benzyl chloride is readily obtained by the solution reaction of the corresponding benzyl alcohol with hydrochloric acid at ambient temperatures.

The preferred benzyl chloride is 4-hydroxy-3,5-ditertiary-butyl-benzyl chloride.

Salts of Thiocyanic Acid

Any inorganic salt of thiocyanic acid can be reacted with the hydroxy dialkyl benzyl halide to produce the corresponding thiocyanates. Sodium thiocyanate, strontium thiocyanate, potassium thiocyanate, and ammonium thiocyanate may be mentioned by way of nonlimiting example. Potassium thiocyanate is the preferred inorganic salt reactant.

Preparation of Hydroxy Dialkyl Benzyl Thiocyanate

The reaction between the inorganic thiocyanate salt reactant and the benzyl chloride reactant can be effected in several ways, such as, for example, by fusing the reactants. Suitably, the reaction can be effected by refluxing a mixture of the hydroxy dialkyl benzyl chloride reactant and an excess of the inorganic salt reactant neat or in a solvent, such as acetone, at a temperature of between 0° to 150° C., preferably 50° to 100° C. for between 0.25 and 5 hours.

The 4-hydroxy-dialkyl benzyl thiocyanate, preferred is the 4-hydroxy-3,5-di-tert-butyl-benzyl thiocyanate, has utility as an antioxidant for fuels and oils.

The Hydroxy Dialkyl Benzyl Alkyl Thiocyanato Salt/Thiourea

The product of the invention can be readily prepared from hydroxy dialkyl benzyl thiocyanate by reaction with an oil-soluble alkyl primary amine.

Useful amines are those compounds characterized by a radical having the structural configuration $R-N-H_2$ with wherein R represents a $C_{12}$ to $C_{24}$ linear alkyl group or a branched alkylene group containing 12 to 24 total carbons according to the formula [isobutylene]$_n$ wherein n has a value of from 3 to 6. Thus the useful amines are monoamines having from 12 to 24, preferably 16 to 20 carbons, optimally having branched chains.

The optimal amines can be fully characterized by the formula

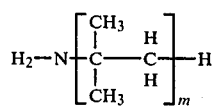

wherein m ranges from 4 to 5.

The preferred amines include a branched alkyl primary amine believed to have 16 to 18 carbon atoms in the alkyl chains which is sold as Primene JMT by Rohm and Haas of Philadelphia, PA.

USE OF THE ADDITIVE IN HYDROCARBON COMPOSITIONS

The thiocyanate and thiocarbamyl reaction products of this invention can be incorporated into a wide variety of hydrocarbon compositions. They can be used in lubricating oil compositions, such as automotive crankcase lubricating oils, automatic transmission fluids, etc., in concentrations generally within the range of about 0.01 to 20 wt.%, e.g. 0.1 to 10 wt.%, preferably 0.3 to 3.0 wt.%, of the total composition. The lubricants to which the products of the invention can be added include not only hydrocarbon oils from petroleum, but also include synthetic lubricating oils such as polyethylene oils; alkyl esters of dicarboxylic acid; complex esters of dicarboxylic acid, polyglycol and alcohol; alkyl esters of carbonic or phosphoric acids; polysilicones; fluorohydrocarbon oils; mixtures of mineral lubricating oil and synthetic oils in any proportion, etc.

When the products of this invention are used in petroleum fuels such as gasoline, kerosene, diesel fuels, No. 2 fuel oil and other middle distillates to provide antirust properties, a concentration of the additive in the fuel of from 4 to 20 parts per million based on the weight of the total composition, will usually be employed.

The additives of the invention may be conveniently dispensed as an additive concentrate of from 20 wt.% to 80 wt.% with the balance conventionally a mineral lubricating oil e.g. up to 80 wt.%, with or without other additives being present.

In the above compositions or concentrates, other conventional additives may also be present including dyes, pour point depressants, antiwear agents such as $P_2S_5$-treated terpene or zinc dialkyl dithiophosphates of 3 to 8 carbon atoms in each alkyl group, antioxidants such as N-phenyl-α naphthylamine, tert-octylphenol sulfide, 4,4'-methylene bis (2,6-di-tert-butyl phenol), viscosity improvers such as ethylene-propylene copolymers, polymethacrylates, polyisobutylene, alkyl fumarate-vinyl acetate copolymers and the like, deemulsifiers such as polysiloxanes, ethoxylated polymers and the like.

The invention will be further understood by reference to the following examples, which include preferred embodiments of the invention.

EXAMPLE 1

4-hydroxy-3,5-di-t-butyl-benzyl chloride 176 grams of 4-hydroxy-3,5-di-tert-butyl-benzyl alcohol was slurried in 350 ml of hexane. 240 cc of concentrated HCl was added to the slurry and stirred overnight. The two phases were allowed to separate and the hexane phase washed twice with water. The dried hexane was then extracted with magnesium sulfate and filtered. Rotofilm evaporation yielded 168 grams of product—a pungent yellow liquid.

EXAMPLE 2

4-hydroxy-3,5-di-tert-butyl-benzyl thiocyanate 127 grams of (0.5 moles) of the product of Ex. 1 was stirred with 80 grams (0.8 moles) of potassium thiocyanate dissolved in 750 ml of acetone. The acetone was removed by blowing air across the stirred reactants and the mixture triturated with water in the blender. The filtered off solids were dissolved in ether, washed once with water, separated, dried and filtered. The ether was blow off, the solids triturated with hexane, filtered and dried in a vacuum oven over the weekend. The yield was 118 grams of a yellow solid.

Preparation of the $C_{16}$-$C_{20}$ t-alkyl primary amine 4-hydroxy-3,5-di-tert-butyl-benzyl thiocyanato/thiourea.

EXAMPLE 3

8.1 grams (0.03 moles) of Primene JMT sold by Röhm and Haas, Philadelphia, PA and believed to be a mixture of $C_{16}$-$C_{20}$ t-alkyl primary amines was combined with 8.3 grams (0.03 moles) of the product of Ex. 2 in xylene and refluxed at 144° C. for 6 hours. The mixture was the washed twice with 50 ml of water, dried with magnesium sulfate, filtered and rotofilmed. A yield of 14.3 grams of a dark, red viscous liquid was obtained.

EXAMPLE 4

The process of Example 3 was carried out except that the reactants were stirred overnight at ambient temperatures. The product obtained here had the same IR as that of Example 3. Analysis gave 3.01 wt.% nitrogen.

EXAMPLE 5

To evaluate in part the utility of the products of the invention, the product of Ex. 3 was subjected to the Falex Shear Test for measurement of antiwear activity.

1% by weight of the product of Example 3 was dissolved in Solvent 150 N mineral oil by stirring for 45 minutes at room temperature. The blend was evaluated in a Falex apparatus wherein the test pins are weighed before and after each run. The results obtained are shown hereafter in Table I.

TABLE I

| Test No. | Additive of Example | Product Wt. % | mg loss under test conditions of 250 lbs. for 2 min. followed by 500 lbs. for 28 min. |
|---|---|---|---|
| 1 | — | 0 | sheared off |
| 2 | 3 | 1.0 | 3.9 |
| 3 | 3 | 1.0 | 4.6 |
| 4 | 3 | 0.5 | 2.8 |
| 5 | 4 | 0.5 | 3.5 |
| 6 | zinc dialkyl dithiophosphate | 0.5 | sheared off |

The difference in weight, i.e. grams lost during test conditions reflects the enhanced antiwear and extrene pressure properties provided to the oil by the additives of the invention.

EXAMPLE 6

A fully formulated SAE 10W 40 lubricating oil was prepared by blending zinc dialkyl dithiophosphate, 1 wt.% of the additive of Example 4 and a sulfonate-phenate detergent-dispersant package in a mineral lubricating oil. The formulation was tested in a ASTM Sequence 3-D engine test. The 3-D test evaluates the oxidation characteristics of the oil blend as measured by viscosity change. After 64 hours the test blend showed 63% viscosity increase (passing limit is 300% increase) at 40° C.

EXAMPLE 7

When the product of Example 4 was evaluated for friction modification of a fully formulated SAE 30 grade blend in a ball-on-cylinder test, the blend containing 0.2 wt.% of said product had a 64% lowered friction coefficient i.e. from 0.33 to 0.12, with noticeable reduction of wear.

It is to be understood that the Examples present in the foregoing specification are merely illustrative of this invention and are not intended to limit it in any manner; nor is the invention to be limited by any theory regarding its operability. The scope of the invention is to be determined by the appended claims.

What is claimed is:

1. A hydrocarbon composition comprising a major amount of a liquid hydrocarbon and a minor but at least anti-wear amount of a hydrocarbon-soluble sulfur-nitrogen-containing additive being the equimolar reaction product of a 4-hydroxy-di($C_1$-$C_4$ alkyl) benzyl thiocyanate and an oil soluble primary amine having the structural configuration R-N-$H_2$ where R represents a $C_{12}$ to $C_{24}$ linear alkyl group or a branched alkylene group containing 12 to 24 total carbons according to the formula (isobutylene)n where n has a value of from 3 to 6.

2. A hydrocarbon composition according to claim 1 wherein said hydrocarbon is a mineral lubricating oil and said amount of said additive is from 0.01 to 20 weight percent of the total weight of said composition.

3. A hydrocarbon composition according to claim 1 wherein said hydrocarbon is a fuel and said amount of said additive is from 4 to 20 parts per million based on the total weight of said composition.

4. A hydrocarbon composition according to claim 2 wherein said alkyl primary amine has 16 to 20 total carbons and said thiocyanate is 4-hydroxy-3,5-di-tertiary-butyl benzyl thiocyanate.

5. The equimolar reaction product of a 4-hydroxy-di-($C_1$-$C_4$ alkyl) benzyl thiocyanate and an oil-soluble primary amine having the structural configuration R-N-$H_2$ wherein R represents a $C_{12}$ to $C_{24}$ linear alkyl group or a branched alkylene group containing 12 to 24 total carbons according to the formula [isobutylene]$_n$ wherein n has a value of from 3 to 6.

6. An oil additive concentrate comprising a mineral oil containing 20 to 80 weight percent of the product of claim 5.

7. The concentrate of claim 6 wherein the alkyl primary amine has 16 to 20 total carbons and said thiocyanate is 4-hydroxy-3,5-di-tertiary butyl benzyl thiocyanate.

* * * * *